United States Patent [19]

Adams et al.

[11] Patent Number: 5,132,210

[45] Date of Patent: * Jul. 21, 1992

[54] DIAGNOSTIC TEST FOR STAPHYLOCOCCAL MASTITIS

[75] Inventors: D. Scott Adams; Travis C. McGuire, Jr., both of Pullman, Wash.

[73] Assignee: ProScience Corporation, Sterling, Va.

[*] Notice: The portion of the term of this patent subsequent to Jul. 18, 2006 has been disclaimed.

[21] Appl. No.: 364,372

[22] Filed: Jun. 12, 1989

Related U.S. Application Data

[63] Continuation-in-part of Ser. No. 936,750, Dec. 2, 1986, Pat. No. 4,849,341.

[51] Int. Cl.$^5$ .................. G01N 33/569; C07K 15/04
[52] U.S. Cl. ........................ 435/7.33; 435/4; 435/29; 435/36; 435/820; 435/883; 436/501; 436/518; 436/811; 530/350; 530/825
[58] Field of Search .............. 435/4, 29, 36, 7.33, 435/7.93, 7.95, 883, 240.27, 820; 436/518, 547, 548, 501; 530/350, 387

[56] References Cited

U.S. PATENT DOCUMENTS 4,425,330 1/1984 Norcross et al. .............. 424/92
4,849,341 7/1989 Adams et al. .............. 435/7

OTHER PUBLICATIONS

Davis A. et al., Journ. Biol Chem. 252 No. 18:6544-6553 (1977).
Gudding, R., Acta. Vet. Scand. 21:242-255 (1980).
Adams et al, "*Staphylococcus aureus* Antigens Reactive with Milk Immunoglobulins G of Naturally Infected Dairy Cows" J. Clin. Microbiol 26(6) pp. 1175-1180 Jun. 1988.
Sevier et al. "Monoclonal Antibodies in Clinical Immunology" Clin Chem 27(11) pp. 1797-1805 1981.
Oellerich, "Enzyme-Immunoassay: A Review" J. Clin chem Clin Biochem. 22 pp. 895-904 1984.

*Primary Examiner*—Esther L. Kepplinger
*Assistant Examiner*—Carol E. Bidwell
*Attorney, Agent, or Firm*—Iver P. Cooper

[57] ABSTRACT

The present invention relates to (1) an enzyme-linked immunosorbent assay (ELISA) for detection in milk of antibodies of any isotype which are specific for *Staphylococcus aureus* proteins in molecular weights ranging from 14,000 to 26,000 daltons, (2) a process for production and purification of the proteins, (3) a method of performing the ELISA utilizing the proteins (4) use of the ELISA for detection of intramammary infection by *S. aureus,* (5) preparation of monoclonal and polyclonal antibodies against the selected fractions, (6) use of such antibodies of purification of infection specfic antigens, and (7) use of the antibodies in an ELISA for antibodies produced in an individual in response to infection by *S. aureus.*

34 Claims, 5 Drawing Sheets

DIAGNOSTIC TEST FOR STAPHYLOCOCCAL MASTITIS

CROSS-REFERENCE TO RELATED APPLICATION

This application is a continuation-in-part of U.S. Ser. No. 06/936,750, filed Dec. 2, 1986, now patented, U.S. Pat. No. 4,849,341, from which priority is claimed, and incorporated by reference herein.

BACKGROUND OF THE INVENTION

1. Field of the Invention

This invention relates to an *S. aureus* specific intramammary infection (mastitis) assay.

2. Information Disclosure Statement

*Staphylococcus aureus* is an important pathogen of humans and animals. In dairy cattle, it is the most frequent cause of mastitis which is the most costly disease of food producing animals in the United States. *S. aureus* persists in infected cows and usually cannot be eradicated from the mammary gland by antimicrobial therapy. Therefore, persistently infected cows are important reservoirs and shedding of the organism contributes to the spread of infection to other cows.

Bovine mastitis is an inflammation of the bovine mammary gland or udder. While mastitis is most often caused by *Staphylococcus aureus*, it is also attributable to many other organisms including *Streptococcus agalactiae*, Pseudomonas spp., certain coliform bacteria and mycoplasmas. Mastitis damages the udder and lowers milk production, and therefore imposes an economic burden on the dairy industry. In view of the complex etiology of mastitis, the optimum treatment course may not be apparent until the organism is identified. This is typically done commercially by culturing the organism and classifying it by conventional taxonomic procedures.

*Staphylococcus aureus* is extremely complex from an immunological standpoint, and a variety of staphylococcal antigens have been studied as potential reagents in immunoassays for staphylococcal antibodies in milk or sera. These include antibodies against protein A, see Live and Ranu, J. Bacteriol., 96:14–23 (1968); enterotoxins, see Fey, et al., J. Clin. Microbiol., 19:34–38 (1984); hemolysins, see Spencer, et al., Am. J. Vet. Res., 24:83–98 (1963); Surujballi and Fackrell, J. Clin. Microbiol., 19:394–98 (1984); Opdebeeck, et al., Am. J. Vet. Res., 43:1770–75 (1982); Christensson, et al., Acta Path. Microbiol. Immunol. Scand., Sec B, 91:351–56 (1983); crude capsular antigens, see Opdebeeck and Norcross, Am. J. Vet. Res., 46:1561 (1985); Watson and Davies, Res. Vet. Sci. 1985, 39:52–58; whole bacteria, see Mathison, et al., Am. J. Vet. Res., 45:2518–24 (1984); teichoic acid, see Granstrom., J. Am. Microbiol., 17:640–46 (1983); peptidoglycan, see Christensson, et al., J. Clin. Microbiol., 19:680–86 (1984); leukocidin, See Loeffler and Norcross, Am. J. Vet. Res., 46:1728 (1985); and nucleases, see Gudding, Acta. Vet. Scand., 21:1–14 (1980).

Human patients with deep-seated *S. aureus* infections have serum antibodies to staphylococcal antigens which can be used for diagnostic purposes. Several tests using different antigens and test formats are described, the most common test being the detection of antibody to *S. aureus* specific teichoic acid.

Mammary gland secretions of the cow contain immunoglobulins of blood and local origin that may have diagnostic potential. Further, a number of workers have shown that active infection of the mammary gland by *S. aureus* and/or immunization with *S. aureus* and/or immunization with *S. aureus* antigens induce specific immunoglobulins detectable in blood and milk.

Norcross and Obdebeeck, U.S. Pat. No. 4,425,330, used *Staphylococcus aureus* strain Wood 46 to produce a staphylococcal alpha hemolysin, which they crudely purified by the method of Coulter, J. Bacteriol., 92:1655–62 (1966). This preparation was then used as an ELISA reagent. Similar use was made of "staphylococcal somatic antigen", essentially a crude sonicate of the cells.

Our invention is distinguished from that of Norcross and Obdebeeck by the fact that it uses highly purified antigens with a limited molecular weight range, preferably 18,000 to 26,000 daltons. The significance of their use in an immunological reagent is that virtually all *S. aureus* infected cows have antibodies in their milk which bind these antigens. Such antibodies are lacking in the milk of uninfected cows. The antigen preparation does not contain alpha or beta hemolytic activity or significant quantities of polysaccharide.

Immunoassays have been developed for the detection of antibodies to specific *Staphylococcus aureus* antigens. Christensson, et al., Acta Path. Microbiol. Immunol. Scand., Sect. B, 91:351–356 (1983) (alpha and beta hemolysin); Loeffler and Norcross, Am. J. Vet. Res., 46:1728–32 (1985) (leukocidin); Gudding (1980), supra, (nucleases).

Gudding (1980), supra, discloses use of *Staphylococcus aureus* nuclease in immunoassays of milk and serum. An allegedly statistically significant difference was found between the titres of *S. aureus* antinucleases in the milk and serum of cows diagnosed as having clinical *S. aureus* mastitis and the titre in cows which had not been so diagnosed. There was no significant difference between cows diagnosed as having "Staphylococcus aureus latent infection" and those diagnosed as having "infectious mastitis" caused by other microorganisms.

Over 90% of the infected cows examined by the assay of the present invention for immunological reaction between their milk and the disclosed antigenic preparation were subclinical, that is, they showed no visible signs of clinical mastitis, even though their milk exhibited the presence of *Staph. aureus* when cultured. The assay of Gudding, et al. (1980), unlike our own assay, failed to distinguish subclinical *Staph. aureus* mastitis ("latent infection") and mastitis caused by other microorganisms. As seen in Gudding Table 2 the titer for subclinical cases averaged 8.7, and for non-Staph. mastitis, 8.6. Gudding speculated that his ability to detect clinical Staph. mastitis was a result of epithelial breakdown, permitting increased transfer of antibody molecules from blood to milk (page 251).

The main commercial method for detecting staphylococcal mastitis is bacterial culture, which has several disadvantages. It detects only live bacteria and therefore antibiotic residues may interfere with detection. It is often inaccurate because of contamination and, therefore, requires that a sterile sample be obtained. It is labor intensive and time consuming. It costs about 10 times as much per sample as the present invention.

The molecular weights of some of the staphylococcal protein antigens are as follows: alpha hemolysin (36,000), beta hemolysin (33,000), gamma hemolysin (45,000) leucocidin (31,000), enterotoxin A (34,700);

enterotoxin B (28,366), enterotoxin C (34,100), enterotoxin C[2] (34,000), enterotoxin E (29,600), enterotoxin F (20,000) and protein A (41,000). See Mollby, in Staphylococci and Staphylococcal Infections, at 644-645 (Easman and Adlam, eds: 1983), Vol. 2.

The industry lacks an enzyme-linked immunosorbent assay (ELISA) and method for detecting specific antibodies to a purified antigen fraction of S. aureus.

SUMMARY OF THE INVENTION

The present invention relates to assays for Staphylococcus aureus antibodies in body fluids, especially milk, of mammals, especially bovines and humans In one embodiment, the assays employ Staphylococcus aureus exoprotein antigens which are more likely to be found in Staphylococcus aureus-infected subjects than in other subjects. Such antigens may be characterized by their molecular weight; only antigens within a particular weight range have the desired specificity. For use in assays, these antigens may be immobilized or labeled. In a second embodiment, these antigens are used to raise antibodies which may be immobilized or labeled for use as assay reagents.

Unlike other assays for S. aureus antibodies, it does not employ a single species of antigen, such as a nuclease, a hemolysin, a leukocidin, etc. Rather it employs, in a preferred embodiment, essentially all S. aureus exoprotein antigens in a particular molecular weight band of at least 2Kd width, said band being selected on the basis of its ability to discriminate between S. aureus-infected subjects and other subjects. Preferred bands include the 14-26, 18-26 and 22-26 Kd bands.

Nor does the present assay employ all S. aureus exoprotein antigens, as do other methods known in the art. Antigens below 14Kd or above 38Kd are excluded. Preferably, antigens above 26 Kd are also dispensed with.

Using the fractionated antigens of the present invention, polyclonal and monoclonal antibodies have been made which usefully compete with S. aureus antibodies in milk for the binding sites of the fractionated antigen, and these antibodies have been used to purify S. aureus-infection-specific antigens by affinity chromatography techniques. The present invention thus embraces both sandwich and competitive immunoassays using the antigen and antibody reagents described herein, as well as the reagents per se and methods for their production.

The claims appended hereto incorporated by reference herein as an enumeration of the preferred embodiments.

DETAILED DESCRIPTION OF THE INVENTION

This invention is a sensitive and specific test of intramammary infection that can be used for clinical diagnostic purposes. The invention uses purified antigens of S. aureus selected on the basis of their ability to bind antibodies in the milk of infected mammals, which are preferably cows, and their failure to react immunologically with antibodies in the milk of non-infected mammals. This invention is described in its application to cows, but this description is not intended to exclude the adaptation of this invention to other mammals, especially humans.

The antigenic preparation of the present invention comprises less than all Staphylococcal aureus exoproteins, and is limited to exoproteins of particular molecular weights. Preferably, the preparation is substantially free of exoproteins of less than 14KD or more than 34KD; exclusion of exoprotein of molecular weights above 26KD is more preferred since they contribute to false positive results. The preparation should contain at least one non-nuclease antigen, especially a non-nuclease, nonhemolysin antigen. Preferably, it contains substantially all exoproteins of molecular weights 22-26KD, especially 24-26KD. More preferably, it contains substantially all S. aureus exoproteins from 14-26KD. The invention is not limited to any particular process for obtaining the desired fraction or infection-specific antigens thereof.

Purification of the antigen can be performed alternatively by ultrafiltration, polyethylene glycol concentration, ion exchange, or salting out, or, using a suitable monoclonal or polyclonal antibody as later described, the antigens can be purified by immunoaffinity chromatography directly from the supernatant.

For use in an assay for S. aureus antibodies, the fractionated antigen may be immobilized on a suitable support, such as a microplate or bead, or it may be tagged with a suitable label.

In a "sandwich assay", the sample antibody forms a ternary complex with an immobilized binding partner for the antibody and a labeled binding partner (which may be the same or different) for the antibody. At least one of these binding partners is the fractionated S. aureus antigen described herein. The other may be an S. aureus antigenic reagent, an anti-antibody (e.g., a goat antihuman antibody when assaying for S. aureus antibodies in human body fluid), or other substance having a binding affinity for antibody (e.g., protein A of Staphylococcal aureus or protein G of Streptococci). The antiantibody can be isotype-specific, species-specific, or merely immunoglobulin specific. The complex may be formed by simultaneous incubation of the sample with both the solid phase and labeled reagents, or by sequential incubation in either order, with or without intermediate separation of bound and unbound components.

In a "competitive assay", the sample antibody may be forced to compete with a labeled anti-Staphylococcus antibody for the binding sites of fractionated staphylococcal antigen according to the present invention. Preferably, in this case the antigen is immobilized. Alternatively, sample antibody may be compelled to compete with a solid phase antibody for a labeled antigenic reagent. More complex competitive formats are also known in the art. Again, the incubations may be sequential or simultaneous.

While HRPO is the preferred label, other labels known in the immunoassay art, including non-enzymatic labels such as fluorescent and radioactive labels, may be employed. The label can be directly attached to the antigen or antibody, or an indirect means such as an antibody-antigen, carbohydrate-lectin, or biotin-avidin bridge can be used. The assay format can be changed so that bound and unbound components are distinguishable without the need for physical separation.

Numerous enzyme immunoassay formats, labels conjugation and immobilization techniques, etc., are disclosed in the following publications, hereby incorporated by reference herein: O'Sullivan, Annals Clin. Biochem., 16:221-240 (1976); McLaren, Med. Lab. Sci., 38:245-51 (1981); Ollerich, J. Clin. Chem. Clin. Biochem., 22:895-904 (1984); Ngo and Lenhoff, Mol. Cell. Biochem., 44:3-12 (1982). The present invention is directed generally to the use of the disclosed antigens and antibodies in assays for S. aureus antibodies in body fluids of infected subjects and is not limited to any particular form of immunoassay.

While the present invention especially relates to the use of the size-fractionated S. aureus antigens to detect antibodies in milk, it can also be used to screen other body fluids, such as serum and urine, or other biological fluids such as culture media, for the presence of the same or similar antibodies. Moreover, while the assay is particularly suited to the detection of staphylococcus-related mastitis in cattle, it can also be used, with the same (or with different, but similarly selected) antigens, for the detection of staphylococcal infections in other mammals, especially humans.

In one embodiment, exoprotein antigens of S. aureus having apparent molecular weights of 14-26 KD were purified by molecular sieving and PAGE-SDS. Cows with intramammary S. aureus infection had antibody in their milk to the 14-26 KD exoproteins. In contrast, milk from the cows with no intramammary infection with S. aureus had little, if any, detectable antibody to these antigens; provided that the sample was taken 30 days or more postpartum and while the cows were producing 13.6 kg of milk or more per day.

These proteins can conveniently be used in an enzyme-linked immunosorbent assay for detection of antibodies signifying intramammary infection by S. aureus, when present in milk.

With such an assay, it is possible to adopt an appropriate therapy for the infected cows, since the assay will not be positive if the mastitis is attributable to infection by, e.g., Streptococcus agalactiae or by Mycoplasma spp.

EXAMPLE 1

Obtaining S. Aureus Exoproteins

The Wood-46 strain of S. aureus, obtained from the American Type Culture Collection (ATCC 10832), is maintained frozen in broth or on blood agar base (Difco) Six-hundred microliters of an overnight culture (grown in CCY medium) of Wood-46 is added to 1 liter of CCY liquid medium consisting of 40 g casein hydrolysate, 10 g dialyzed yeast extract, 20 g Na beta glycerophosphate, 10 ml 50% Na lactate, 1 g $Na_2HPO_4$. $H_2O$, 0.4 g $KH_2PO_4$, 1 g$(NH_4)SO_4$, 80 mg DL-tryptophan, 100 mg L-cystine and q.s. to 1000 ml with distilled $H_2O$. This is autoclaved together at 15 PSI for 30 minutes. To this is added 10 ml of a solution containing 20 mg thiamine and 40 mg nicotinic acid in 100 ml of distilled $H_2O$ (previously autoclaved separately). Ten ml of a solution of trace elements (also autoclaved separately) which contains 0.2 g $MgSO_4$. $7H_2O$, 0.1 g $MnSO_4$. $4H_2O$, 0.06 g $FeSO_4$. $7H_2O$ and 0.06 g citric acid in 100 ml of $dH_2O$ is also added to the large volume (Wooden, A. W., Biochemistry. J. 73: 225-237, 1959). The bacteria are grown under aerobic conditions for 24 to 48 hours either with shaking or by bubbling filtered air through the medium. Cultures are checked for purity by streaking on blood agar: tests for coagulase activity and latex agglutination (prothrombin/IgG coated), and a Gram's stain, are performed on the subculture. The cells are removed from the CCY medium by centrifugation at 1500 xg for 20 minutes and the supernatant is retained. Other media can be used, which can alter the relative production of the different exoproteins or which can simplify subsequent purification of the proteins from the medium.

S. aureus exoproteins were screened with 12 milk samples (4 S. aureus positive, 4 coagulase negative staphylccoccus positive and 4 noninfected) in an ELISA. Milks from the S. aureus positive animals had antibodies which reacted with the unfractionated exoproteins (TABLE 1A, below). Two milk samples from the coagulase negative staphylococci-infected cows and one sample from the noninfected cows had antibodies that reacted, resulting in optical densities of more than 0.100.

TABLE 1A

| | Anti $G_1$ | |
|---|---|---|
| S. aureus Infected | Coagulase Negative Infected | Uninfected |
| 0.461 | 0.118 | 0.009 |
| 0.317 | 0.016 | 0.046 |
| 0.604 | 0.006 | 0.017 |
| 0.499 | 0.145 | 0.109 |

Theorizing that milk antibodies from the S. aureus infected cows were recognizing different antigens than the milk antibodies from the other groups, the exoproteins were fractionated by size using a G-200 Sephadex column and SDS-PAGE so as to maintain the infection specific antigens and remove the non-specific components. Table 1B indicates the infection specificity of the fractionated antigen, whose purification is described in the next section.

TABLE 1B

| | Anti $G_1$ | |
|---|---|---|
| S. aureus Infected | Coagulase Negative Infected | Uninfected |
| 0.328 | 0.038 | −0.010 |
| 0.338 | 0.003 | 0.002 |
| 0.249 | −0.008 | −0.013 |
| 0.377 | 0.004 | −0.004 |

Purification of the 14 to 26 KD Exoproteins

A. Concentration and Ultrafiltration

Phenylmethylsulfonyl fluoride (0.13M in acetone, Sigma) to a final concentration of 1 mM and N-alpha-p-tosyl-1-lysine chloromethyl ketone (Sigma) as powder to a final concentration of 0.1 mM are added to the supernatant. The supernatant is dialyzed against a buffer of 50 mM Tris (Sigma) (pH 8.0) containing protease inhibitors, 0.01 mM phenylmethylsulfonyl fluoride, 0.001 mM N-alpha-p-tosyl-1-lysine chloromethyl ketone, 0.05 mM (ethylenedinitrilo)-tetraacetic acid (disodium salt) (Mallinckrodt) and 0.05 mM iodoacetamide (Sigma) and alternatively concentrated by evaporation in a fume hood through 5 to 6 changes of buffer until the volume inside the dialysis tubing (10 KD cutoff) is approximately 1/30th the original volume. The solution inside the tubing is then centrifuged for 30 minutes at 1500 x g and the supernatant is filtered through a 0.20 micron filter.

B. Gel Filtration Chromatography

Sample (38 ml) containing 1.47 mg/ml of protein according to Bradford, *Anal. Biochem* 72:248 (1976), was placed on a 500 ml column packed with Sephadex G-200 (Sigma Chemical Co., St. Louis, MO) and equilibrated in 0.15M phosphate buffered saline, pH 7.5 with protease inhibitors. Four ml fractions were collected, assayed by enzyme-linked immunosorbent assay (ELISA) as described below and a pool made of material eluting between 316 and 376 ml. This pool was placed in dialysis tubing and concentrated by evaporation to approximately 6.5 ml containing 1 mg/ml protein.

Five sequential antigen pools were made and tested in ELISA versus the 12 milk samples (TABLE 2).

TABLE 2

Reactions of Milk Antibody in ELISA to Concentrated Fractions of *S. aureus* Exoproteins Eluted from Sephadex G-200 Matrix.[a]

| Elution Volume | S. aureus Infected Cows[b] | Coagulase Negative Staphylococci Infected Cows | Culture Negative Cows |
|---|---|---|---|
| 136–200 ml | 0.219 ± 0.140 | 0.177 ± 0.107 | 0.060 ± 0.060 |
| 224–264 ml | 0.152 ± 0.071 | 0.116 ± 0.121 | 0.080 ± 0.043 |
| 268–312 ml | 0.139 ± 0.067 | 0.053 ± 0.021 | 0.038 ± 0.024 |
| 316–376 ml | 0.285 ± 0.063 | 0.049 ± 0.021 | 0.027 ± 0.018 |
| 380–544 ml | 0.122 ± 0.053 | 0.040 ± 0.070 | 0.025 ± 0.028 |

[a] All eluates were diluted to 10 microgram/ml of protein in coating buffer
[b] Mean ± standard deviation of optical densities of 4 cows, n = 4

All 5 pools reacted with antibodies in milk from the *S. aureus* infected cows with an optical density lower than for the unfractioned exoproteins. However, one fraction, 316–376, conferred the best differentiation between infected and noninfected cows.

C. SDS-PAGE

A portion of the material from the Sephadex G-200 column was then subjected to polyacrylamide gel electrophoresis with sodium dodecyl sulfate (Bio-Rad, Richmond, CA) (PAGE-SDS) in a 1.5 mm vertical slab gel apparatus (Hoefer Scientific, San Francisco, CA) containing a 15% polyacrylamide resolving gel and 5% stacking gel according to Laemmli, Nature 227:680 (1970). The antigen solution (0.25 mg) was diluted to 1 ml in 50 mM Tris, pH 8.0, mixed with an equal volume of sample buffer containing 2-mercaptoethanol (Sigma Chemical Co., St. Louis, MO) as a reducing agent and boiled. Prestained standard proteins (Lysozyme 14.3 KD, Beta lactoglobulin 18.4 KD, alpha chymotrypsinogen 25.7 KD, ovalbumin 43.0 KD, bovine serum albumin 68.0 KD, phosphorylase B 97.4 KD, myosin [H-chain] 200.0 KD from Bethesda Research Laboratories, Gaithersburg, MD) were run simultaneously in separate lanes at each end of the slab with the power supply set at 130 v and 30 ma until the tracking dye was 10 cm from the top of the resolving gel.

Seven horizontal strips (6 mm wide) were cut from the sample lane beginning at the middle of the 14.3 KD standard and going upward. The seven strips were placed inside dialysis tubing with 6 ml of buffer and electrophoresed perpendicular to the long dimension of the gel at 30 v and 75 to 100 ma for 3 hours. The buffer in the tubing and the chamber was 25 mM TRIS, pH 8.3 containing 0.192M glycine (J. T. Baker Chemical Co., Phillipsburg, NJ).

The concentrated exoproteins, G-200 eluates and the eluates from PAGE-SDS electroeluted eluates were screened for reactivity utilizing milk samples in an ELISA. Twelve wells of Immulon 1 (Dynatech Laboratories, Chantilly, VA) styrene microtiter plates were coated with 0.05 ml of antigens for 3 hours at 37° C. The exoproteins and G-200 elutes were diluted for coating the wells in 0.1M carbonate/bicarbonate buffer, pH 9.6 and the PAGE-SDS eluates were diluted in the electroelution buffer described above. The wells were blocked with 0.05 ml PBS containing 0.2% azide and 0.5% BSA (Sigma Chemical Co., St. Louis, MO) for 2 hours at 37° C. The plates were then washed 3 x with PBS containing 0.05% Tween 20 (J. T. Baker Chemical Co., Phillipsburg, NJ). Milk samples from 4 *S. aureus* infected, 4 coagulase negative staphylococcus infected and 4 noninfected (culture negative on blood agar as described below) cows were diluted 1:2 in PBS containing 0.2% azide, 0.5% BSA and 0.05% Tween 20 and 0.5 ml of each was added to each of the 12 wells corresponding to each strip. The plates were incubated for 30 minutes at 37° C. and then washed 4 X with the same buffer as above. A 1:500 dilution of horseradish peroxidase-labeled anti-bovine $IgG_{1,2}$ (V..M.R.D., Inc., Pullman, WA) in PBS containing 0.5% BSA and 0.5% Tween 20, 0.05 ml was added to each well and incubated for 30 minutes at 37° C. After washing 3 x, 5 amino-salicylic acid (Sigma Chemical Co., St. Louis, MO) was added and incubated at room temperature for 1 hour. The optical densities were determined spectrophotometrically at a wave length of 490 nm.

TABLE 3 shows the reactivity of the various size fractions eluted from the PAGE-SDS strips.

TABLE 3

ELISA Reactivity of Milk Antibody to Fractions of *S. aureus* Antigens Eluted from Polyacrylamide Gel

| Apparent Molecular Weight of Fraction | S. aureus Infected Cows | Coagulase Negative Staphylococci Infected Cows | Culture Negative Cows |
|---|---|---|---|
| 34–38 kd | 0.478 ± 0.178[a] | 0.025 ± 0.013 | 0.061 ± 0.023 |
| 30–34 kd | 0.151 ± 0.136 | 0.008 ± 0.011 | 0.006 ± 0.004 |
| 26–30 kd | 0.275 ± 0.183 | 0.008 ± 0.009 | 0.006 ± 0.006 |
| 22–26 kd | 0.421 ± 0.150 | 0.007 ± 0.007 | 0.005 ± 0.004 |
| 18–22 kd | 0.347 ± 0.182 | 0.020 ± 0.013 | 0.019 ± 0.003 |
| 14–18 kd | 0.309 ± 0.066 | 0.018 ± 0.010 | 0.018 ± 0.005 |
| <14 kd | 0.023 ± 0.026 | 0.003 ± 0.004 | 0.005 ± 0.006 |
| Buffer Only | 0.006 ± 0.009 | 0.000 ± 0.004 | 0.002 ± 0.002 |

[a] Mean ± standard deviation of 4 cows to 2 eluates, n = 8

The best differentiation between *S. aureus* infected and uninfected cows was obtained with the three antigenic fractions having apparent molecular weights in the range of 14–26 Kd, the best of these being 22–26 Kd. The *S. aureus* infected cows reacted most strongly to the 34–38 Kd fraction, but that fraction had relatively high reactivity with samples from uninfected cows. Very little activity was found in fractions above 38 Kd.

Eluates causing the highest optical densities when reacted with milk samples from *S. aureus* infected cows and the lowest optical densities with milk samples from coagulase negative staphylococci infected cows and noninfected cows were pooled for use an antigen for testing Groups A through F milk samples described below.

It was discovered that the "active fraction" of this invention can have activity from 18 to 34 KD when DEAE is used to replace the G-200 column in the purification scheme. This spreading can be attributable to post translational modifications caused by proteolytic enzymes of *S. aureus*.

Differentiating Ability of Purified Exoproteins from "Alpha" and "Beta Toxin" Isolates While Wood-46 is the preferred strain, other strains can be employed, particularly those considered likely to be the mastitis-causing agents in the region of interest.

Both "Wood-46" and "Alpha Toxin" strains were grown under identical conditions and concentrated exoproteins of each were tested for their ability to inhibit in the ELISA described herein. As a rule the "alpha toxin" isolate produces 5 to 10 fold greater inhibition than Wood-46 strain on a per mg of protein basis. While all of about 30 strains of *S. aureus* tested seem to produce inhibition, no strain other than "alpha toxin" has produced greater inhibition than Wood-46.

The exoprotein preparation from the "alpha toxin" strain was carried through the antigen purification process and it was found that the active fraction is also between 18 and 26KD but tends to have greatest activity nearer 18KD than Wood-46. It can be that the critical antigen(s) of "alpha toxin" are of slightly lower molecular weight than those of Wood-46. However due to the fact that they inhibit specific binding of antibody to the Wood-46 derived proteins it is assumed that the antigenic epitopes are substantially similar or identical.

While the 18-26 KD fraction of the "alpha toxin" strain is more reactive with *S. aureus* antibodies than the corresponding fraction of Wood-46 exoproteins, the latter is preferred because Wood-46 is a long-cultivated strain of unquestioned availability and stability.

Selection of Milk Samples for Screening Mastitis-Related Antigenic Preparations

The operating hypothesis for this example was that cattle with intramammary infection by *S. aureus* secrete antibodies into milk that can be detected by ELISA provided that the correct antigen preparation is used.

In order to insure that antigen(s) of sufficient ubiquity among *S. aureus* populations are selected to render the test sensitive and that antigen(s) of sufficient uniqueness are selected to render the test specific, it was necessary to classify milk samples into two carefully defined categories: 1 - samples from cows with intramammary *S. aureus* infection and 2 samples with no evidence of intramammary *S. aureus* infection. To do this, somatic cell counts and bacterial cultures were performed on milk samples from Holstein dairy cows on a monthly basis. The following summarizes our observations:

- *S. aureus* was isolated from some cows on a single or just a few occasions and often without elevation of somatic cell counts. It became clear, as others have found (Dodd, F. H., National Mastitis Council Meeting, February, 1986), that merely isolating *S. aureus* from milk samples of cows without elevation of the somatic cell counts is insufficient evidence of intramammary infection. These isolations of *S. aureus* are apparently due to contaminations of samples from/by personnel and/or the environment or due to infections distal to the mammary gland itself. These were false positive samples.

- *S. aureus* can be isolated from some cows only periodically but with somatic cell counts sometimes remaining elevated. This phenomenon is, perhaps, due to low grade infections by *S. aureus* in which the organism might be shed only periodically. Negative cultures of these cows were considered false negatives.

In addition, somatic cell counts were generally found to be elevated (greater than 150,000/ml) only in those cows with persistent and, what was assumed to be, intramammary infection. Somatic cell counts in cows without intramammary infection were generally less than 150,000/ml.

Milk samples from 3 different Holstein dairy herds, designated 1, 2, or 3, were used in one study. Composite milk (a pool of milk from the 4 quarters of each cow) samples were collected and 50 microliters of each sample was spread on a 16×100 mm blood agar plate for initial culturing. Following incubation at 37° C. for 24 hours, colony morphology and hemolytic pattern were used to tentatively identify staphylococcal isolates. Non-staphylococcal isolates were further identified according to established procedures (Microbiologic Procedures for Use in the Diagnosis of Bovine Mastitis, 2nd ed., National Mastitis Council, Inc., 1981, Carter Press, Inc., Ames, Iowa). All staphylococcal isolates were gram-stained and tested for catalase and coagulase production. Staph Trac strips (API, Plainview, NY 11803) were also performed to identify all staphylococcal isolates. No attempt was made to isolate Mycoplasma spp.

Composite milk samples had been cultured and somatic cell counts were performed monthly from all lactating animals in the 3 herds for the past year. Prevalence of *S. aureus* infection in each herd used for milk antibody testing was as follows: Herd 1, 3.9%; Herd 2, 14.5%; and Herd 3, 42.3%. Selected milk samples were tested for antibodies to the pooled PAGE-SDS eluate antigens by ELISA for *S. aureus*. Samples from cows in the 3 herds were divided into 5 groups.

Group A included 31 samples from cows defined as having intramammary *S. aureus* infection. These samples were from cows from which *S. aureus* has been consecutively cultured for at least 4 months. The sample chosen for antibody determination was from a culture positive month, but was not taken from the first or the last month in which *S. aureus* was cultured. All Group A samples contained greater then 150,000 somatic cells/ml. Somatic cell counts in this group ranged from 164,000 to 8,493,000 cell/ml. Additionally, all Group A samples were taken 30 days or more after parturition and when the cow was producing more than 13.6 kg of milk per day.

Group B consisted of 37 samples from cows defined as having no evidence of intramammary *S. aureus* infection. These samples were taken from cows which were not infected with *S. aureus* during the current lactation. All Group B samples had somatic cell counts below 150,000 cells/ml. These samples were also taken 30 days or more after parturition and when the cow was producing more than 13.6 kg *Escherichia coli*, 6 coagulase negative staphylococci and the remainder negative.

Group C samples were from 9 cows not infected with *S. aureus* during the lactation in which the sample was taken, but the sample tested for antibody contained greater than 150,000 somatic cells/ml. Milk production was greater than 13.6 kg per day and the cows were greater than 30 days after parturition. Culture results were as follows: 4 coagulase negative staphylococci and the remainder negative.

Group D include 23 samples from cows that were less than 30 days from parturition but were not culture positive for *S. aureus* during the lactation in which the sample was taken. Somatic cell counts in these samples ranged form 29,000 to 1,706,000 cells/ml. Culture results were as follows: 1 *Streptococcus uberous*, 4 coagulase negative staphylococci and the remainder negative.

Group E included 6 samples taken from cows from which coagulase negative staphylococci were consecutively isolated for at least 4 months. The sample tested for antibody to *S. aureus* was not taken from the first or last month in which coagulase negative staphylococci were isolated. The cows were also at least 30 days postpartum and producing more than 13.6 kg of milk per day at the time the sample was taken. Somatic cell counts in this group were 37,000 to 262,000 cells/ml.

Group F consisted of 7 samples from cows with no evidence of *S. aureus* infection but producing 13.6 kg of milk per day or less. The range of somatic cells was 247,000 to 2,211,000 cells/ml. Culture results were as follows: 1 coagulase negative staphylococcus and the remainder negative.

Testing of 14–26 KD Exoproteins As ELISA Reagent in Assay for Staphylococcal Mastitis Antibodies A pool of eluates from the 14 to 26 kd region was made from 2 PAGE-SDS procedures and used to test Group A through F milk samples. Optimal dilution of the pooled antigen in the ELISA was determined to be 1:14 in the elution buffer. Antibody binding to the pooled antigen by the various groups of milk samples are summarized in TABLE 4.

TABLE 4

Reactivity of Antibody in Selected Milk Samples to 14–26 Kilodalton Antigens of *S. aureus* in ELISA.

| Group[a] | Number of Samples | Mean ± SD | Range |
|---|---|---|---|
| A | 31 | 0.332 ± 0.123[b] | 0.089–0.634 |
| B | 37 | 0.014 ± 0.011 | 0.000–0.035 |
| C | 9 | 0.021 ± 0.016 | 0.003–0.051 |
| D | 23 | 0.114 ± 0.158 | 0.001–0.684 |
| E | 6 | 0.020 ± 0.026 | 0.001–0.068 |
| F | 7 | 0.191 ± 0.125 | 0.010–0.370 |

[a]Group A = *S. aureus* infected; Group B = *S. aureus* negative; Group C = *S. aureus* negative with elevated somatic cells; Group D = *S. aureus* negative 30 days or less after parturition; Group E = Coagulase negative staphylococci infected; Group F = *S. aureus* negative less than 13.6 kg/day milk production.
[b]Optical densities Group A (*S. aureus* infected) had the greatest reactivity to the antigen while Group B (noninfected) had the least. There was no overlap in the optical density ranges of these two groups.

Figure 1:
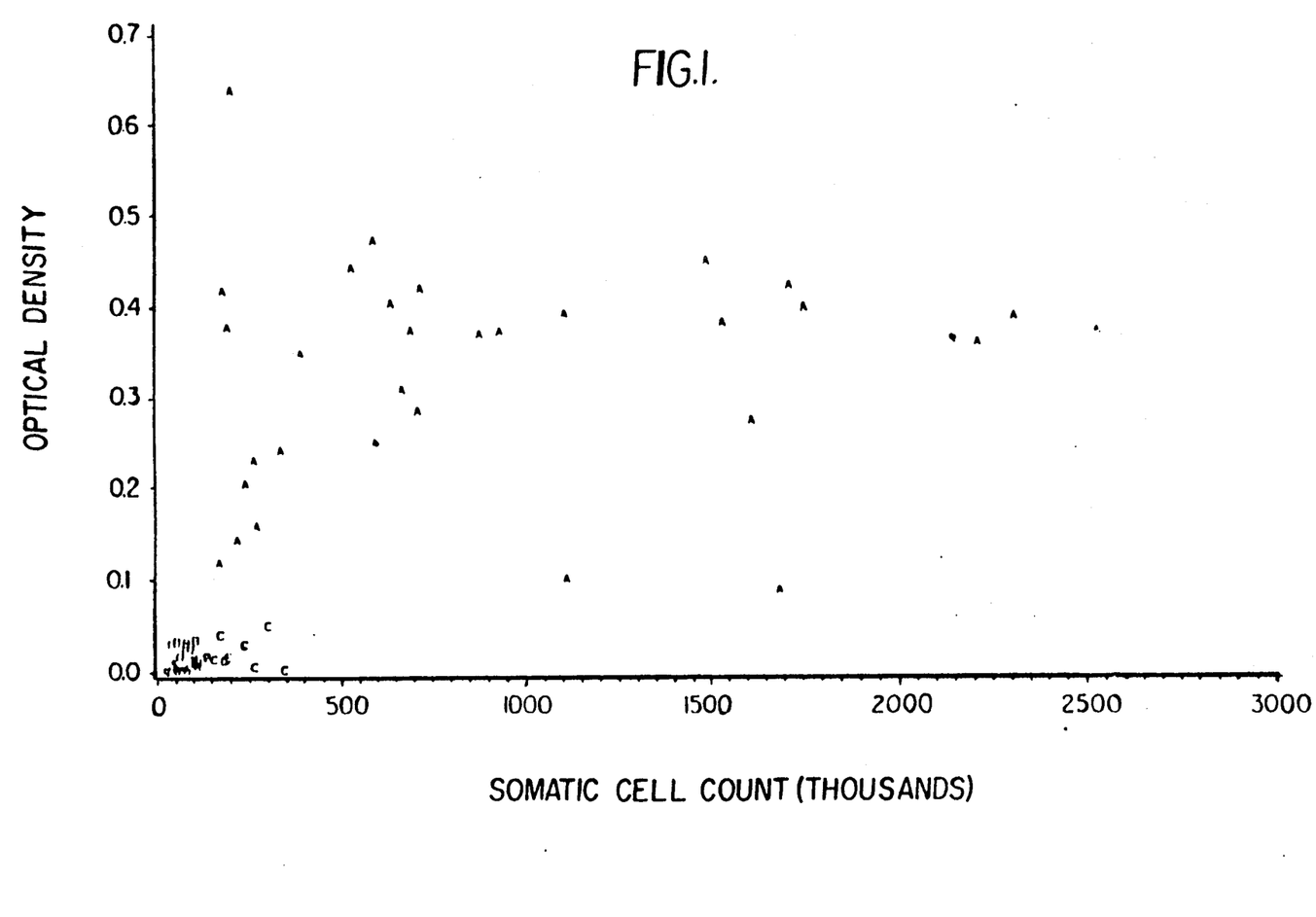
FIG. 1 Optical densities of samples plotted against somatic cell counts from Groups A (S. aureus infected, n=30) B (noninfected, n=37) and C (noninfected with somatic cells above 150,000, n=9)

Group C (elevated somatic cell counts without *S. aureus* infection) was tested in order to determine whether there was a correlation between reactivity to the antigen preparation and elevated somatic cell counts, independent of infection with *S. aureus*. There was no overlap in the ranges of Groups A and C. FIG. 1 illustrates a lack of relationship between somatic cell count and optical density in Groups A, B and C. The pooled within group correlation was low (r=0.109).

Group D was evaluated because it was observed in preliminary experiments that milk samples from some *S. aureus* negative cows which were less than 30 days postpartum were reactive to the antigen. These observations are confirmed by the data in FIG. 2 which presents the optical densities of *S. aureus* negative Groups B, C and D plotted against the number of days in milk. Seven samples from cows less then 30 days partum elicited optical densities of greater than 0.1 indicating the presence of antibody reactivity.

Samples from cows infected with coagulase negative staphylococci (Group E) were tested to determine if this infection induced antibodies cross reactive with the 14–26 15 kd *S. aureus* antigens. There was no overlap in optical densities between Group E and Group A, indicating very little cross reacting antibody.

Figure 3:
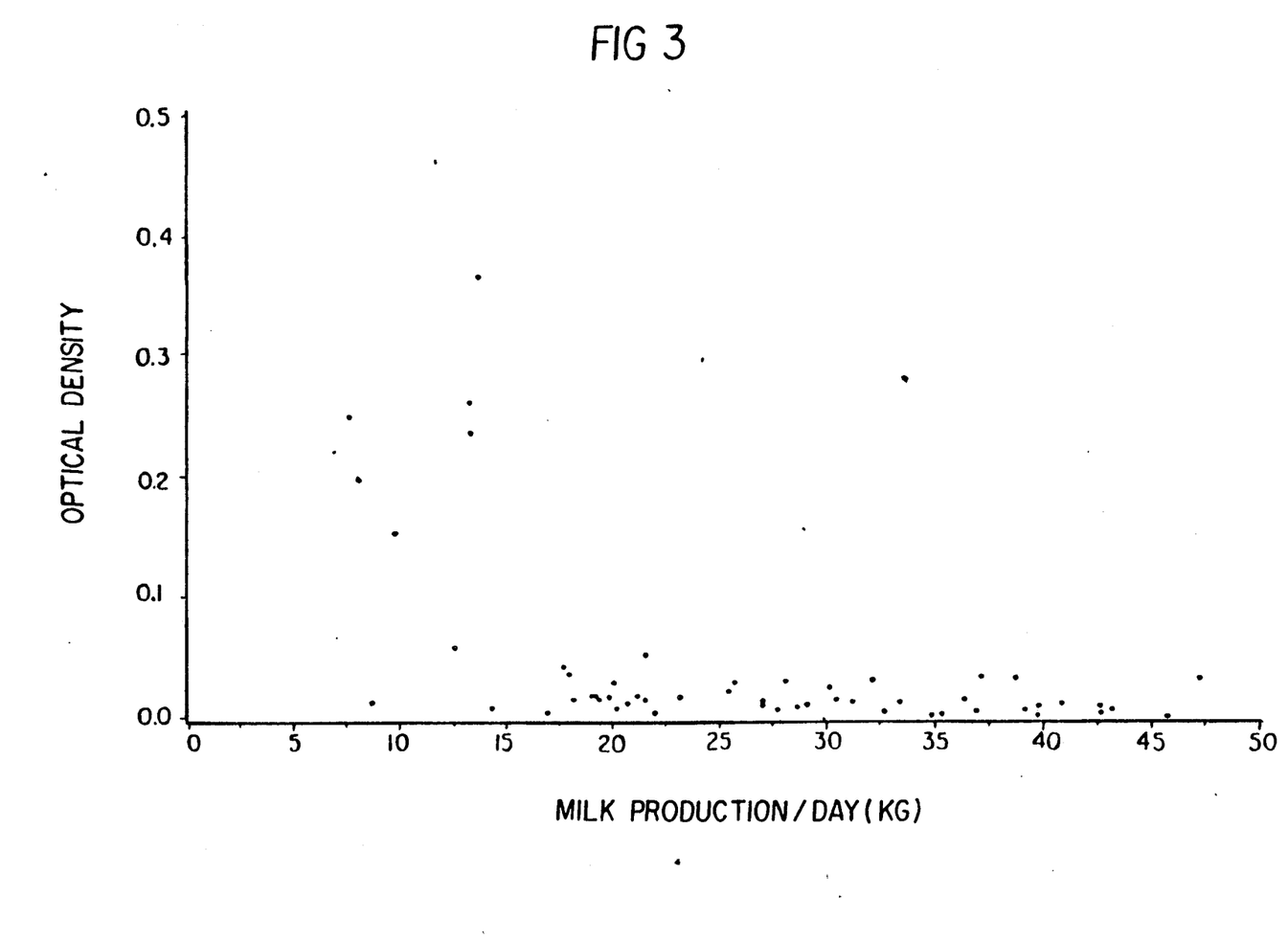
FIG. 3 Optical densities of samples from noninfected cows (Group B, C, and F, n=53) plotted against milk production.
Figure 4:
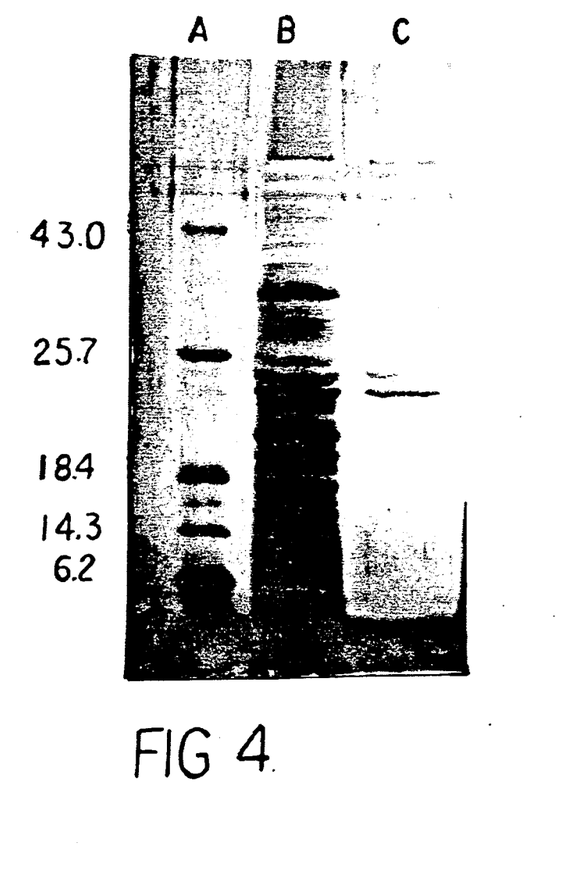
FIG. 4 Molecular weight standards (Lane A). Silver Stain of PAGE-SDS S. aureus exoproteins after Sephadex G-200 chromatography (Lane B) and of 14 to 26 KD eluate used for ELISA to detect antibodies in milk (Lane C).

Group F cows had milk production below 13.6 kg/day. Antibody against the antigens could be detected in some of these samples despite the apparent absence of intramammary infection by *S. aureus*. FIG. 3 shows the optical densities of *S. aureus* negative Groups B, C and F plotted against pounds of milk/day.

Milk from some cows less than 30 days postpartum (Group D) without detectable intramammary *S. aureus* infections, had antibody which bound the antigen preparation. These results can be explained by the observation that $IgG_1$ passes from the blood into the milk during the prep and postpartum periods. The presence of *S. aureus* antigen specific antibody in the blood in cows lacking intramammary infections was most likely due to previous infection or current infection at a location other than the mammary gland. The presence of antibodies specific for the *S. aureus* antigens in the milk of some noninfected cows producing less than 13.6 kg of milk per day (Group F) can also be explained by the passage of $IgG_1$ from the blood into mammary secretions during involution of the mammary gland.

Lack of reactivity to the *S. aureus* antigens by milk samples (Group E) from cows infected with coagulase negative staphylococci suggests that this infection does not induce detectable antibody in the milk to the 14 to 26 kd exoantigens of *S. aureus*. Because coagulase negative staphylococci are more closely related to *S. aureus* than other bacteria, this finding is considered to be strong evidence for the specificity of the isolated 14–26 kd antigens.

Additionally, it is possible that other micro-organisms exist which might cause false positive reactions either by production of cross-reacting antigens or through mechanisms of vascular damage in which *S. aureus* antibodies might leak into mammary secretions from the blood. The latter situation could occur with acute coliform infections. With a limited number of samples from cows with this type of infection, false positive reactions have not been observed.

Milk from cows with *S. aureus* infection have high somatic cell counts and most noninfected cows more than 30 days post-partum and producing more than 13.6 kg of milk per day have low somatic cell counts. The range of reactivity of *S. aureus* negative cows with elevated somatic cell counts was low (0.003–0.051). The data base for this example had very few noninfected cows with elevated somatic cell counts that were more than 30 days postpartum and producing than 13.6 kg of milk per day. Nevertheless, the results suggest that elevation of somatic cells alone, without infection by *S. aureus* is not a cause of false positive reactions in the test. In support of this was a lack of correlation between somatic cell counts and optical density in Group A samples (*S. aureus* infected) with somatic cell counts up to 2,600,000 cells/ml (FIG. 1).

Figure 2:
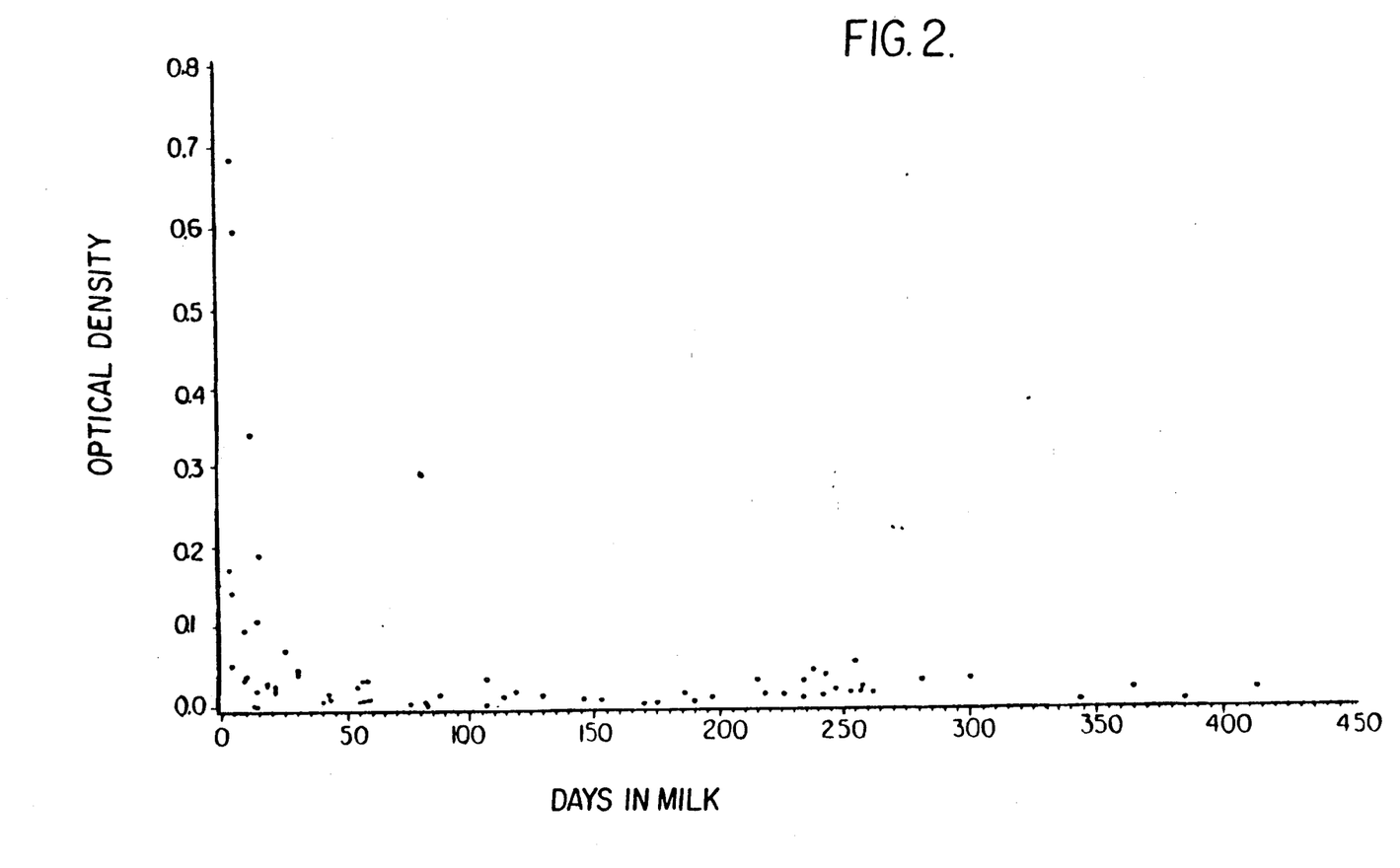
FIG. 2 Optical densities of samples from noninfected cows (Group B, C and D, n=69) plotted against days in milk.

The purpose of the initial test on Herds 1-3 was to determine the best parameters for maximum sensitivity and specificity of the ELISA relative to culture. The ELISA reactivity relative to SCC, stage of lactation, and milk production is illustrated in FIGS. 1 through 3.

*Staphylococcus aureus* culture positive sample (Group A) had by far the highest average ELISA reactivity of all groups. Furthermore, there was no overlap of ranges between culture positive and culture negative groups provided that the *S. aureus* culture negative samples came from cows that were more than 30 days in milk and producing more than 13.6 kg. of milk/day (Groups B, C, and E). Correlation with culture was 100% with Groups A, B, C, and E. As shown in Table 4B, samples from some culture negative cows (Groups D and F), which were less than 30 days in milk or producing less than 13.6 kg of milk/day, exhibited *S. aureus* specific antibody. There was no apparent relationship between SCC and antibody activity (Table 4B, Group C and FIG. 1).

Based on the data from Herds 1-3 criteria were established to determine whether a sample was positive or negative for specific antibody to *S. aureus* by the ELISA. There were as follows: a positive sample had to be greater than 3 standard deviations above the means of a panel of negative control samples and greater than a weak positive control; antibody positive samples which came from cows less than 30 days in milk or producing less than 13.6 kg. of milk/day were downgraded to "suspect."

An additional 94 cows from 5 herds (Herds 4-8) were sampled and cultured in most cases once but some were sampled and cultured twice. The ELISA was performed on the same sample which was used for culture data. Eighty-four samples were aseptically collected from Herd 9 and divided into two aliquots. One was cultured and potassium dichromate was added to the other on which the ELISA was performed.

Dual samples, one for culture and one for DHIA, were collected from all milking cows of 4 more herds (Herds 10-13). The DHIA sample was collected from the milk meter by DHIA personnel and preserved with either potassium dichromate or 2-bromo-2-nitropropane-1, 3-diol. These samples were shipped to the DHIA laboratory for routine tests and then to VMRD, Inc., N.W. 115 State, Pullman, Washington 99163 where the ELISA was performed. There were 347 dual samples tested from herds 10-13. A few cows from these herds were later sampled and cultured again.

Herds 4-13 were tested with the ELISA according to the above criteria. "Suspects" were not included in these data.

For Groups A, B and C of Herds 1-3 (77 samples) and Herds 4-13 (525 samples), a total of 602 samples from 602 different cows, the sensitivity was 93%, the specificity was 99% and the overall accuracy was 98% relative to bacterial culture.

TABLE 5

Comparison of ELISA and Culture for Herds 1-13.

| | ELISA + | ELISA − | TOTAL |
|---|---|---|---|
| *Staphylococcus aureus* Culture | +132 | 10 | 142 |
| | −4 | 456 | 460 |
| TOTAL | 136 | 466 | 602 |

Accuracy for samples preserved with potassium dichromate or 2-bromo-2-nitropropane-1, 3-diol (herds 9-13) was not significantly different from the accuracy obtained with unpreserved samples. Neither did collecting, shipping, and handling of samples through DHIA laboratories (Herds 10-13) adversely affect accuracy.

Among the 10 samples that were negative by ELISA for antibody and positive for *S. aureus* by culture, 8 had SCC's of less than 300,000 ml. Of the 4 samples that were positive by ELISA for antibody to *S. aureus* but negative by culture for *S. aureus*, SCC's were 512,000, 50,000, 257,000 and 1,143,000 ml. Culture results on these samples were *Streptococcal* spp. (non-Str. agalactiae) and coliforms, culture negative, *Escherichia coli*, and *Klebsiella* spp., respectively. The latter sample was serosanguinous. Of the 456 samples that were negative by ELISA for antibody to *S. aureus*, 105 were culture positive for an organism other than *S. aureus*, as follows: 84 coagulase negative staphylococci, 7 *Streptococcus agalactiae*, 5 *Streptococcus* spp. (non-*Streptococcus agalactiae* 4 non-hemolytic coagulase positive staphylococci, 2 *Klebsiella* spp., 2 coliforms and 1 *Serratia* spp..

The 4 ELISA false positive reactions found in the 456 *S. aureus* culture negative samples can indicate any of the following: minor-cross reactivity of the purified *S. aureus* antigen preparation with antigens of other organisms; leakage of blood *S. aureus* antibodies into the milk due to trauma, perhaps from another infection; covalescent antibody from a previous intramammary infection with *S. aureus;* or failure to culture *S. aureus* from the milk in spite of a current intramammary infection. The 105 samples that were culture positive with other organisms and antibody negative strongly suggest that cross-reactivity, if it exists, is not a significant problem. The sample from which *Klebsiella* spp. was isolated was serosanguinous suggesting that blood antibody was present in the sample. The herd from which the sample came also had a high rate of *S. aureus* infection which suggests that the cow from which the sample may have been exposed to *S. aureus*.

There were 10 samples from which *S. aureus* was isolated but antibody could not be detected. Seven of these cows were re-sampled and cultured positive on the second sampling. The SCC in most of these cows was not particularly high. Therefore, it may have been that these were either early infections or infections not involving the gland's secretory tissue, for instance, the teat end, streak canal or teat cistern. In such cases, there might not have been sufficient antigenic stimulation to promote formation and secretion of detectable *S. aureus* antibody into the milk. In support of this, we have observed that some antibody negative/culture positive cows spontaneously recover from the infection with time.

The ELISA of this invention offers a new and useful diagnostic tool for the dairy industry to control one of its most costly pathogens, *Staphylococcus aureus*. It is accurate, inexpensive, fast, amenable to screening large numbers of samples and offers, for the first time, mastitis pathogen diagnosis on individual cows from preserved DHIA milk samples.

EXAMPLE 2: ELISA ASSAY FOR MASTITIS-RELATED ANTIBODIES

Essentially the same assay format is used for screening milk samples for mastitis-related antibodies, using the antigens of this invention, and for screening test antigens for possible assay use, using milk samples previously tested using a validated technique.

In the ELISA of this invention, the antigen was passively bound to a polystyrene plate, and exposed to the milk sample. The specific antibody in the milk binds to the antigen. Non-binding components are removed by washing and a horseradish peroxidase-labeled, isotype-specific anti-bovine Ig conjugate is added. A substrate is then provided to the peroxidase, resulting in a detectable product.

Dynatech Immulon 1 plates are coated with 0.05 ml of antigen for 3 hours at 37° C. and blocked by adding 0.05 ml PBS containing 0.2% azide and 0.5% bovine serum albumen for 2 hours at 37° C. The plates are then washed 3 x with PBS containing 0.05% Tween 20. Milk samples are diluted 1:2 in PBS containing 0.2% azide, 0.5% BSA and 0.05% Tween and 20 and 0.05 ml is added to the wells. The plates are incubated for 30 minutes at 37° C. and then washed 4 x with the same buffer as above. A 1:500 dilution of anti-bovine $IgG_{1,2}$ is diluted in PBS containing 0.5% BSA and 0.05% Tween 20 and 0.05 ml is added to each well to incubate for 30 minutes at 37° C. After washing 3 x with wash buffer the substrate (5 amino-salicylic acid) is added. The optical densities are determined spectrophotometrically at a wave length of 490 nm.

EXAMPLE 3

This example describes the antigen effects of sodium dodecyl sulfate (SDS). Test performance can vary depending on the amount of SDS present in the antigen preparation. The following example provides the optical density (O.D.) of positive/negative milks.

TABLE 6

| Optical Density of Positive/Negative Milks for SDS-Treated Antigen Preparations. | | | |
|---|---|---|---|
| | SDS | | |
| | 0.1% | 0.01% | 0.001% |
| Antigen Prep. | 1.797/0.465 | 1.418/0.324 | 0.873/0.188 |
| Antigen Prep. | 0.496/0.113 | 0.721/0.062 | 0.811/0.155 |

The optimal amount of SDS varies with the antigen preparation. It has been found that the addition of 0.01% SDS to diluents and coating buffers "stabilizes" the antigen preparations. It is assumed that this is because the micelle formation is critical and/or the SDS coats the vessels that contain the antigen and prevents it from falling out and/or coating the vessel.

EXAMPLE 4

This example describes the production of monoclonal antibody affinity purified antigen. A monoclonal antibody derived from a mouse immunized with the 14-26 KD antigen preparation reacts in the ELISA to the 14-26 KD antigen preparation and to 1-3 bands in the 24 KD region of a Western blot.

Using this monoclonal antibody, an antigen preparation was purified by affinity chromatography. Crude antigen from the supernatant of the bacterial growth media was used, thus eliminating the molecular sieve, SDS PAGE and electroelution steps of the original antigen purification process.

EXAMPLE 5: Characterization of the Selected Antigenic Fractions

Silver staining of the fraction from molecular sieving before elution from PAGE-SDS demonstrates that a large number of proteins are present. The proteins eluted from PAGE-SDS which had the best reactivity with milk from S. aureus infected cows are from a fairly narrow molecular weight range between 14 and 26 kd and the most visible ones are in the 24-26 kd range. There have been a number of S. aureus proteins of 14 to 26 kd described including staphylokinase at 13-15 kd, nuclease at 16.8 kd, pyrogenic toxin B at 18.0 kd, enterotoxin F at 20.0 kd, lymphocyte mitogen at 21.0 kd, gamma toxin at 26.0 kd and beta toxin at 26.0 kd.

Unfractionated exoproteins purified from Wood-46 cultures were significantly more S. aureus infection-specific than unfractionated exoproteins purified from "alpha toxin" and "beta toxin" isolates provided to us by Dr. Norcross. These are believed to correspond to his "Dutchess" and "Sprint" isolates. These bacteria were grown in CCY medium, and the pure exoproteins were concentrated and dialyzed as previously described. No further purification was carried out.

TABLE 6A

| | "Beta Toxin" Exoproteins Run 1 (anti $G_1$) | |
|---|---|---|
| S. aureus Infected | Coagulase Negative Infected | Uninfected |
| 0.282 | 0.224 | 0.028 |
| 0.083 | 0.025 | 0.051 |
| 0.375 | 0.011 | 0.004 |
| 0.250 | 0.056 | 0.072 |

Below are the initial screening results using purified exoproteins from the "alpha toxin" isolate.

TABLE 6B

| | "Alpha Toxin" Exoproteins Anti $G_1$ | |
|---|---|---|
| S. aureus Infected | Coagulase Negative Infected | Uninfected |
| 0.128 | 0.081 | 0.016 |
| 0.024 | 0.009 | 0.041 |
| 0.158 | 0.009 | 0.009 |
| 0.033 | 0.033 | 0.024 |

These may be compared with the data for unfractionated (Table 1A) and fractionated (Table 1B) Wood-46 exoproteins, as given above.

With monoclonal antibody technology, anti-idiotype antibodies could be used to replace the antigen on the plate. A replica of the specific epitope(s) could be made by peptide synthesis or by expression of the DNA coding for the antigens in an expression vector.

These antigens can also have utility in a vaccine preparation for S. aureus-infected cattle.

Nuclease activity of various fractions have been determined by the toludine blue DNA agar method of Lachia, et al., Appl. Microbiol. 21:585-87 (1971).

Figure 5:
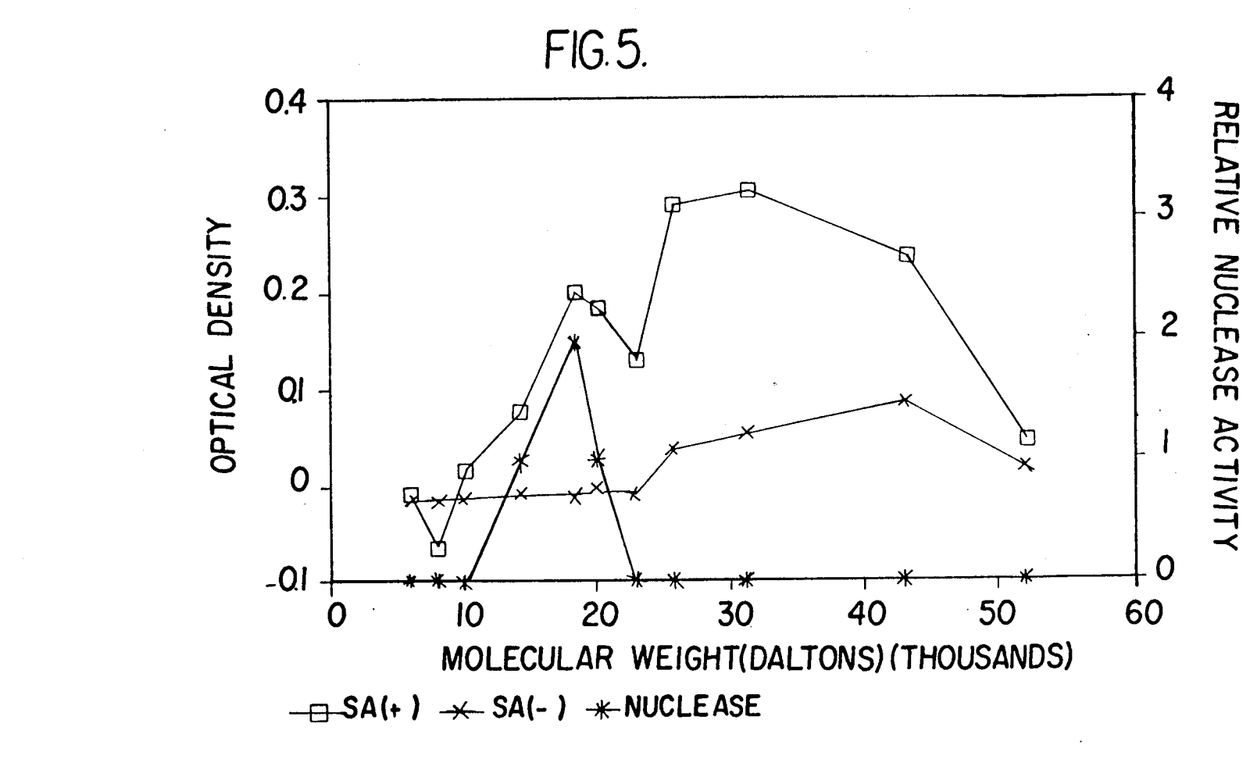
FIG. 5 Plots optical density of Staphylococcus aureus positive and negative samples, as well as nuclease activity, against molecular weight of the eluate.

FIG. 5 shows antibody binding ((optical density) and relative nuclease activity) of S. aureus exoproteins of various molecular weights. The peak nuclease activity is at 18.4 Kd, with some activity at 14.3 Kd and 20.1 Kd. There was no detectable nuclease activity in eluates at any other molecular weight. Since there is significant infection-specific antibody activity above 20.1 Kd, it is clear that the present preparation includes infection-specific, non-nuclease antigens.

EXAMPLE 6

Proteins from the gels were transblotted to nitrocellulose paper (Schein) in transfer buffer (0.025M Tris, 0.192M glycine and 20% methanol in distilled H$_2$O pH 8.9) in a transblot cell (Biorad) overnight at 125 ma. Nitrocellulose paper was blocked with 6% BSA in 0.05M Tris, 0.15M NaCl pH 7.8 (TBS) for 30 minutes and cut into strips. The strips were incubated with antibody diluted with TBS while being agitated for 30 minutes. The strips were then washed twice with TBS, 15 minutes per wash. Conjugate, protein A-HRPO, diluted 1:1000 in TBS was then incubated with the strips as described above for 30 minutes. The strips were again washed as above in 5 ml of substrate solution (10% 4 chloro-1 naphthol diluted 1:5 in 0.05M Tris pH 7.5 0.2M NaCl with 2 ml of 30% H$_2$O$_2$) is added to each strip and agitated for 15 minutes. Antibody binding is indicated by a horizontal purple-blue color line or lines on the strip.

The antisera from immunized rabbits reacted with the 18-26 Kd antigen fraction in the ELISA as follows:

|      | 1:10  | 1:100 | 1:1000 | 1:10 without antigen |
|------|-------|-------|--------|----------------------|
| R123 | 0.584 | 0.205 | 0.020  | 0.001                |
| R124 | 0.475 | 0.147 | 0.017  | 0.000                |

Western Blot antisera from both rabbits reacted strongly at about 24 Kd with a weaker line at about 25Kd.

Balb-C mice were immunized, as described above for the rabbits, but with 1/10 the dose. Speen cells from the mice were fused with myeloma cells 2 months after the first injection. Bleedings from hybridoma were analyzed by Western Blot only. The blots were performed precisely the same as the blots for the rabbit antisera except that the probe for mouse antibody binding was a biotinylated goat anti-mouse IgG and a streptavidin HRPO with a TBS wash between each reagent. The prefusion bleedings of the mice showed binding in the blots at 24 Kd, 18 Kd or 16 Kd. The ELISA was performed as described above except that the biotinylated goat anti-mouse IgG and streptacidin HRPO were used to detect mouse IgG binding to the solid phase antigen. Hybridoma supernatants were screened with the ELISA those with activity were tested by Western Blot and subjected to cloning procedures. Cloned hybridomas were then a-tested by Western Blot. One clone, 763-1G11-2C9 showed activity at 24-25 Kd by Western Blot.

Ascitic fluid was made by intraperitoneal injection of this clone. Twenty mice were injected with 7.5×10$^5$ cells each.

Seven ml of ascitic fluid was precipitated with 50% saturated ammonium sulfate and dialysed against DEAE starting buffer (0.05M phosphate pH 8.0). Ion exchange chromatography was performed on DEAE and step wise elutions were performed (0.1M, 0.2M, 0.3M, and 0.4M NaCl).

The fall through and 0.1M peaks were pooled and dialysed against CNBr activated Sepharose 4B buffer (0.1M NaCO$_3$+0.5M NaCl). According to Pharmacea instructions, the monoclonal protein (132 mg) was attached to gm of activated CNBR Sepharose 4B.

After washing 55 ml (1.5 mg/ml of staphylococcal exoproteins were added to the column and allowed to bind. The column was exhaustively washed with PBS and 1M NaCl and then with PBS alone. Then to elute the 24-25 Kd proteins attached to the monoclonal antibody on the beads, KCN in PBS was added stepwise at 0.5M, 1.0M, 2M and 4M. Peaks from 0.5-4M KCN PBS were pooled and dialysed again using this antigen preparation at 1:40 in an ELISA. Four milks, from culture positive cows, gave the following O.D.'s 0.861, 0.853, 0.772, 0.861 and from six culture negative cows gave O.D.'s of 0.398, 0.084, 0.126, 0.244, 0.757 and 0.033. The second to the last sample was from a cow that had been previously culture positive. The first culture negative sample came from a cow that was producing less than 30 pounds of milk per day.

To determine the amount of inhibiting antigen present in strains of Staph. aureus other than Wood-46, we used an antigen inhibition assay designed as follows. Plates coated with the 18-26 Kd fraction of Staph. aureus antigens were reacted with milk in the usual ELISA format and a standard curve is generated. A dilution of the antibody was chosen which gave an O.D. in the steep part of the dilution curve. Once this O.D. is established the antigen solution in question is mixed with the antibody in a separate vessel and allowed to react for 30 minutes. Then the mixture is transferred to the antigen coated plate and the ELISA is performed as previously described. If enough antigen is present in the first incubation to bind the antibody then the antibody will not be able to bind the antigen on the solid phase.

TABLE 7

Antigen Inhibition Assay of Inhibiting Antigen in Various S. Aureo Strains

| Strain | % Inhibition @ 1 mg/ml |
|--------|------------------------|
| Wood-46 | 16 |
| Alpha-tox | 95 |
| SA 21 | None |
| SA 22 | None |
| SA 244 | 51 |
| SA 90 | 44 |
| Beta-Tox | 46 |
| 466 | None |
| G. V. Andre | None |
| 400 | 74 |
| 148 | None |
| 214 | None |
| 13 | 15 |
| 1 | 5 |
| 4 | 19 |
| 3 | 20 |
| 539 | None |
| OV.11 | 10 |
| OV.33 | None |
| 378 | 11 |
| 247 | 28 |
| 543 | None |
| 153 S. hyicus | None |
| 136 S. hyicus | None |
| 154 | None |
| 124 | 14 |
| 142 S. hyicus | None |
| 128 S. hyicus | None |
| 121 S. xylosus | None |
| 224 | None |
| 145 S. xylosus | None |
| 152 | None |
| 292 S. xylosus | None |
| 290 | None |
| 329 S. xylosus | None |
| 135 S. xylosus | None |

We claim:

1. An immunological reagent comprising a plurality of antigens including a non-nuclease antigen selected from the group consisting of 20 to 24 KD Staphylococcus aureus exoproteins, said reagent being substantially free of Staphylococcus aureus antigens with molecular weights less than about 14 KD or greater than 34 KD.

2. The immunological reagent of claim 1 wherein said antigens are derived from the Wood-46 strain of *Staphylococcus aureus*.

3. The immunological reagent of claim 1 wherein said antigens are essentially free of alpha or beta hemolytic activity and essentially free of polysaccharide.

4. The immunological reagent of claim 1 further comprising substantially all *Staphylococcus aureus* exoprotein antigens of a selected strain of *Staphylococcus aureus* which have molecular weights in the range of 20-24 KD.

5. The immunological reagent of claim 4 wherein the selected strain is the Wood-46 strain.

6. The immunological reagent of claim 4, further comprising substantially all *Staphylococcus aureus* exoprotein antigens of a selected strain of *Staphylococcus aureus* which have molecular weights in the range of 18-26 KD.

7. An immunological reagent comprising substantially all *Staphylococcus aureus* exoprotein antigens of a selected strain of *Staphylococcus aureus* which have molecular weights in the range of 20 to 24 KD and being substantially free of *Staphylococcus aureus* antigens with molecular weights less than about 14 KD or greater than about 34 KD.

8. The immunological reagent of claim 7 wherein said antigens are derived from the Wood-46 strain of *Staphylococcus aureus*.

9. The immunological reagent of claim 7 wherein said antigens are essentially free of alpha or beta hemolytic activity and essentially free of polysaccharide.

10. An immunological reagent comprising at least one staphylococcal mastitis infection-specific *Staphylococcus aureus* exoprotein antigen which is not protein A, an enterotoxin, a hemolysin, teichoic acid, a peptidoglycan, a leukocidin or a nuclease, said reagent being substantially free of antigens with molecular weights less than about 14KD or greater than about 34KD.

11. The reagent of claim 10 wherein the reagent is substantially free of *Staphylococcus aureus* antigens having molecular weights greater than about 26KD.

12. A method of determining whether a mammal of interest is suffering from mastitis by *Staphylococcus aureus* which comprises:
(a) providing the reagent of claim 1 in labeled or insolubilized form, said reagent being substantially more reactive with antibodies in the body fluid of mammals known to have mastitis caused by *Staphylococcus aureus* than with antibodies in the body fluid of mammals known not to have mastitis caused by *Staphylococcus aureus*;
(b) incubating said reagent with a body fluid sample obtained from said mammal of interest;
(c) determining whether antibodies from said sample are bound to the antigens of said reagent; and
(d) correlating the determination of step (c) to mastitis caused by *Staphylococcus aureus*.

13. The method of claim 12 wherein said mammal is a cow and the body fluid is milk.

14. The method of claim 12 further comprising detecting the bound antibodies by means of a labeled antiantibody.

15. The method of claim 12 wherein said antigens are derived from the Wood-46 strain of *Staphylococcus aureus*.

16. The method of claim 12 wherein said antigens are essentially free of alpha or beta hemolytic activity and essentially free of polysaccharide.

17. The method of claim 12 wherein said reagent further comprises substantially all *Staphylococcus aureus* exoprotein antigens of a selected strain of *Staphylococcus aureus* which have molecular weights in the range of 20-24 KD.

18. The method of claim 17 wherein the selected strain is the Wood-46 strain.

19. The method of claim 17 wherein said immunological reagent further comprises substantially all *Staphylococcus aureus* exoprotein antigens of a selected strain of *Staphylococcus aureus* which have molecular weights in the range of 18-26 KD.

20. A method of determining whether a mammal of interest is suffering from mastitis caused by *Staphylococcus aureus* which comprises:
(a) providing the reagent of claim 7, in labeled or insolubilized form, said reagent being substantially more reactive with antibodies in the body fluid of mammals known to have mastitis caused by *Staphylococcus aureus* than with antibodies in the body fluid of mammals known not to have mastitis caused by *Staphylococcus aureus*;
(b) incubating said reagent with a body fluid sample obtained from said mammal of interest;
(c) determining whether antibodies from said sample are bound to the antigens of said reagent; and
(d) correlating the determination of step (c) to mastitis caused by *Staphylococcus aureus*.

21. The method of claim 20 wherein said mammal is a cow and the body fluid is milk.

22. The method of claim 20 further comprising detecting the bound antibodies by means of a labeled antiantibody.

23. The method of claim 20 wherein said antigens are derived from the Wood-46 strain of *Staphylococcus aureus*.

24. The method of claim 20 wherein said antigens are essentially free of alpha or beta hemolytic activity and essentially free of polysaccharide.

25. The immunological reagent of claim 8 wherein said antigens have molecular weights in the range of about 24 and 26 KD.

26. The immunological reagent of claim 1, said antigens are bound to a support.

27. The immunological reagent of claim 1, said antigen are labeled with a detectable label.

28. The method of claim 12, further comprising providing an exogenous antibody which is substantially specific for said reagent, and determining the degree to which said exogenous antibody competes with the antibodies in the sample to bind to said reagent.

29. The immunological reagent of claim 7, wherein said antigens are bound to a support.

30. The immunological reagent of claim 7, wherein said antigens are labeled with a detectable label.

31. The reagent of claim 1 wherein the reagent is substantially free of *Staphylococcus aureus* antigens with molecular weights greater than about 26 KD.

32. The reagent of claim 7 wherein the reagent is substantially free of *Staphylococcus aureus* antigens with molecular weights greater than about 26 KD.

33. The method of claim 12 wherein the reagent is substantially free of *Staphylococcus aureus* antigens with molecular weights greater than about 26 KD.

34. The method of claim 20 wherein the reagent is substantially free of *Staphylococcus aureus* antigens with molecular weights greater than about 26 KD.

* * * * *